US010405834B2

(12) United States Patent
Jaremko et al.

(10) Patent No.: US 10,405,834 B2
(45) Date of Patent: Sep. 10, 2019

(54) SURFACE MODELING OF A SEGMENTED ECHOGENIC STRUCTURE FOR DETECTION AND MEASUREMENT OF ANATOMICAL ANOMALIES

(71) Applicant: The Governors of the University of Alberta, Edmonton (CA)

(72) Inventors: Jacob Lester Jaremko, Edmonton (CA); Abhilash Hareendranathan, Edmonton (CA); Myles Mabee, Edmonton (CA); Richard Thompson, Edmonton (CA); Pierre Boulanger, Edmonton (CA); Kumaradevan Punithakumar, Edmonton (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 15/575,374

(22) PCT Filed: May 31, 2016

(86) PCT No.: PCT/CA2016/050614
§ 371 (c)(1),
(2) Date: Nov. 19, 2017

(87) PCT Pub. No.: WO2016/191870
PCT Pub. Date: Dec. 8, 2016

(65) Prior Publication Data
US 2018/0146953 A1 May 31, 2018

Related U.S. Application Data

(60) Provisional application No. 62/169,530, filed on Jun. 1, 2015.

(51) Int. Cl.
| | |
|---|---|
| *A61B 8/00* | (2006.01) |
| *G06T 7/00* | (2017.01) |
| *A61B 8/08* | (2006.01) |
| *G06T 17/20* | (2006.01) |
| *G06T 7/162* | (2017.01) |
| *G06T 7/11* | (2017.01) |
| *A61B 5/055* | (2006.01) |
| *A61B 6/03* | (2006.01) |
| *G06T 7/12* | (2017.01) |

(52) U.S. Cl.
CPC ............ *A61B 8/5223* (2013.01); *A61B 5/055* (2013.01); *A61B 6/032* (2013.01); *A61B 8/0875* (2013.01); *A61B 8/466* (2013.01); *A61B 8/483* (2013.01); *G06T 7/0012* (2013.01); *G06T 7/11* (2017.01); *G06T 7/12* (2017.01); *G06T 7/162* (2017.01); *G06T 17/20* (2013.01); *G06T 2207/10012* (2013.01); *G06T 2207/10081* (2013.01); *G06T 2207/10088* (2013.01); *G06T 2207/10136* (2013.01); *G06T 2207/20101* (2013.01); *G06T 2207/30008* (2013.01)

(58) Field of Classification Search
CPC ........ G06T 7/0012; G06T 7/12; G06T 7/162; G06T 7/174; G06T 7/55; G06T 7/564; G06T 17/00; G06T 17/20; G06T 2207/20101; G06T 2207/30008; A61B 6/5211; A61B 6/5217; A61B 8/5215; A61B 8/5223
See application file for complete search history.

(56) References Cited

U.S. PATENT DOCUMENTS

| | | | |
|---|---|---|---|
| 9,119,559 B2 | 9/2015 | Collins et al. | |
| 2009/0129673 A1* | 5/2009 | Simon et al. | ......... G06T 7/0012 382/173 |
| 2013/0016092 A1 | 1/2013 | Collins et al. | |
| 2013/0022251 A1* | 1/2013 | Chen et al. | ............ G06T 3/0031 382/131 |
| 2017/0039725 A1* | 2/2017 | Dror et al. | ............ G06T 7/0083 |

OTHER PUBLICATIONS

ISA/CA, "International Search Report" in counterpart PCT application No. PCT/CA2016/050614, dated Aug. 5, 2016.
ISA/CA, "Written Opinion of the International Searching Authority" in counterpart PCT application No. PCT/CA2016/050614, dated Aug. 5, 2016.
Zoroofi et al., "Automated Segmentation of Acetabulum and Femoral Head From 3-D CT Images", IEEE Transactions on Information Technology in Biomedicine, Dec. 2003, vol. 7, Issue 4, pp. 329-343.
Mabee, Mayles Garnet; "Novel Indices for the Diagnosis of Infant Hip Dysplasia using Two and Three Dimensional Ultrasound", Department of Biomediacl Engineering, University of Alberta, 2014.

* cited by examiner

*Primary Examiner* — Andrew W Johns
(74) *Attorney, Agent, or Firm* — ATMAC Patent Services Ltd.; Andrew T. MacMillan

(57) ABSTRACT

An anatomical structure is segmented from images generated in an anatomical scan. A user input device is configured for manually identifying two or more seed points on a plurality of the images. An image processor is configured to identify an optimal path through seed points on the plurality of images with a graph search. The optimal path between corresponding seed points on different images defines a boundary contour, and the anatomical structure includes two or more boundary contour. The image processor is further configured to interpolate the boundary contours over a three-dimensional volume using cardinal splines.

13 Claims, 11 Drawing Sheets

SURFACE MODELING OF A SEGMENTED ECHOGENIC STRUCTURE FOR DETECTION AND MEASUREMENT OF ANATOMICAL ANOMALIES

CROSS-REFERENCE TO RELATED APPLICATIONS

This application claims the benefit of priority of U.S. Provisional Application No. 62/169,530 filed Jun. 1, 2015, which is incorporated herein by reference.

TECHNICAL FIELD

The present invention relates to anatomical imaging. More specifically, the present invention relates to a semi-automatic process for segmenting an echogenic structure and a method for detecting and measuring anatomical anomalies from a surface model generated from the segmented echogenic structure.

BACKGROUND

Recent technological advances have made 3D ultrasound image acquisition practical in many cardiac and non-cardiac clinical settings, but its broad application is limited by difficulties in processing and analyzing the image data. One field in which 3D ultrasound has potential to make a valuable contribution is in assessing developmental dysplasia of the hip (DDH).

DDH is a condition affecting up to 3% of the population in which the acetabulum (the "socket" of the ball-and-socket hip joint) is poorly formed, resulting in a lax and unstable joint prone to premature osteoarthritis. About ⅓ of hip replacement surgeries in patients less than 60 years old are due to DDH. One of the main challenges in diagnosing DDH lies in defining the complex shape deformity of the acetabulum. The conventionally used Graf technique is based on calculating the bony angle ($\alpha$) and cartilage angle ($1$) from 2D ultrasound images. However, this procedure has been criticized for high inter-observer and inter-scan variability. The cause of high inter-scan variance can be attributed to the mono-planar (2D) nature of the approach. Slight variations in the scanning angle can result in vastly different views of the hip joint which results in inconsistent measurement of the a angle.

Automatic segmentation of anatomic structures and lesions from medical ultrasound images is a formidable challenge in medical imaging due to image noise, blur and artifacts. There are multiple techniques for image segmentation in ultrasound. Several segmentation techniques have been applied at the hip joint. Hip segmentation is a tedious and time consuming process mainly due to its complex structure. Unsurprisingly, inter-observer and intra-observer variability are significant during manual segmentation. Several previous studies relied on CT imaging for the segmentation of the hip. For example, in one approach, an automatic segmentation was developed for pelvis and the femur for multi-slice CT data based on thresholds. This approach involved preprocessing steps such as Gaussian smoothing followed by histogram based thresholding. Morphological operations were then used to remove small objects and holes in the segmented image.

Although 3D ultrasound is a radiation-free alternative to CT for hip imaging, automatic techniques for hip joint segmentation are rare in 3D ultrasound. When compared to CT, ultrasound hip volumes contain artifacts such as speckle noise and acoustic shadowing which make it even more difficult to segment the acetabulum and the femoral head. Due to speckle noise, threshold based approaches cannot be extended reliably to ultrasound to date.

SUMMARY

The present disclosure relates to a system and method for segmenting an anatomical structure from images generated in an anatomical scan. A user input device is configured for manually identifying two or more seed points on a plurality of the images. An image processor is configured to identify an optimal path through seed points on the plurality of images with a graph search. The optimal path between corresponding seed points on different images defines a boundary contour, and the anatomical structure includes two or more boundary contour. The image processor is further configured to interpolate the boundary contours over a three-dimensional volume using cardinal splines.

The present disclosure also relates to a system and method for calculating the acetabular contact angle (ACA). Images of a scan of an acetabulum are segmented according to the graph based methodology. A surface of the three-dimensional volume is represented using a polygonal mesh. A first vector defined on the mesh corresponds to the lateral iliac wall and a second vector defined on the mesh corresponds to the acetabular roof. The acetabular contact angle (ACA) is calculated based on an angular separation between the first and second vectors. The ACA can be used to classify the patient's hip, which in turn can be used to determine whether the patient's hip is dysplastic.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
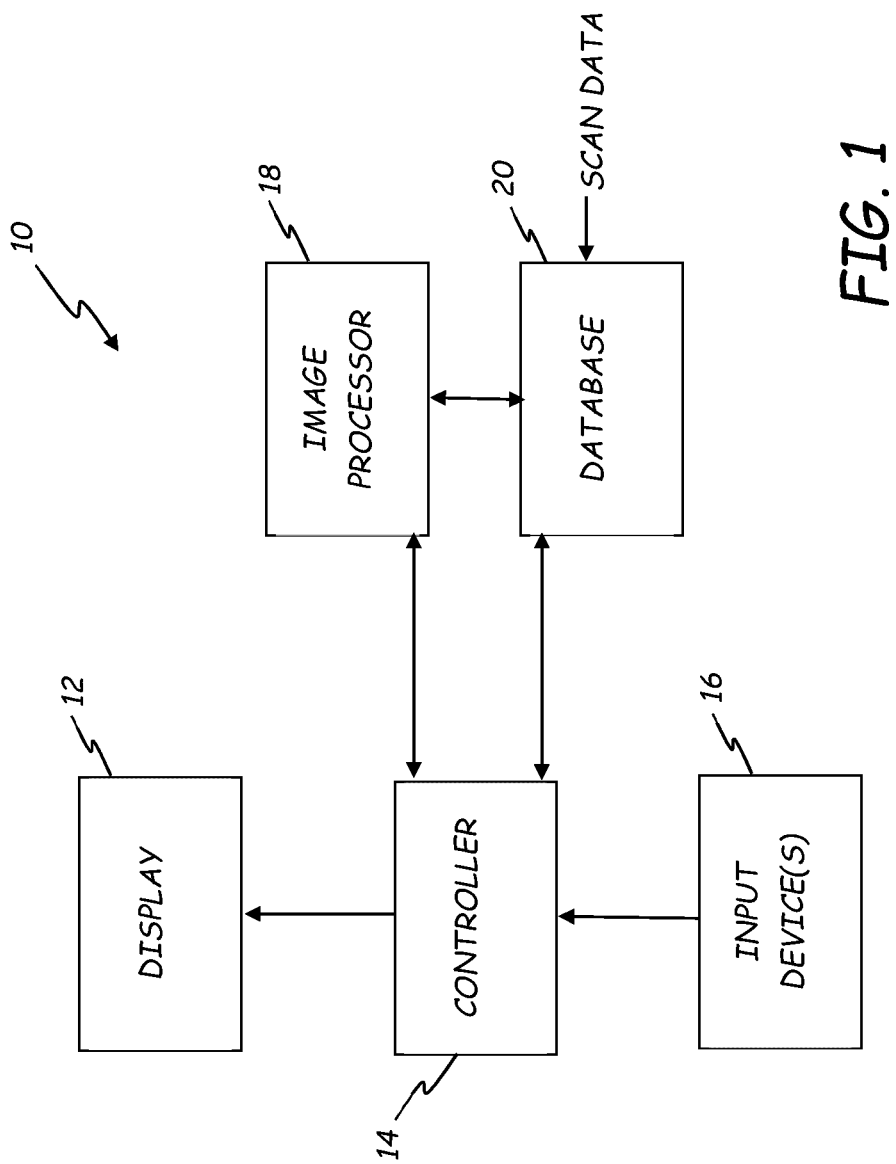
FIG. 1 is a block diagram of an embodiment of a medical imaging system configured to perform the segmentation algorithm of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a block diagram of a medical imaging system 10 including a display 12, a controller 14, one or more input devices 16, an image processor 18, and an image database 20. The controller 14 receives inputs from the one or more input devices 16 and provides an output to the display 12. The display 12, controller 14, and one or more input devices 16 may be configured as a computer workstation, and the one or more input devices 16 may include, for example, a mouse, keyboard, or digital interactive pen. In some embodiments, the input devices 16 are configured to facilitate identifying seed points on a plurality of anatomical scan images. The controller 14 communicates with and controls both the image processor 18 and the image database 20. In some embodiments, the image processor 18 and the image database 20 are located locally with the controller 14. In other embodiments, the controller 14 communicates with and controls the image processor 18 and the image database 20 through the internet, such as via a web-based application run on the controller 14.

The image database 20 receives and stores raw data from one or more scans (e.g., ultrasound) of a patient. The data from the one or more scans may be used by the image processor 18 to generate a moving (cine) image of the scanned anatomical feature or assemble the scans into a three dimensional (3D) image of the anatomical feature being analyzed. The image processor 18 may also isolate an anatomical feature of interest from the surrounding anatomy based on the response of each portion of the anatomy to the scan. For example, the anatomical feature of interest may have a different density (i.e., a different level of transparency to the scan signal) than the surrounding anatomy, and the different portions of the anatomy can thus be separated by the image processor 18 from each other based on this varying level of density. The image processor 18 may then store data related to the assembled 3D medical image in the imaging database 20.

Figure 2:
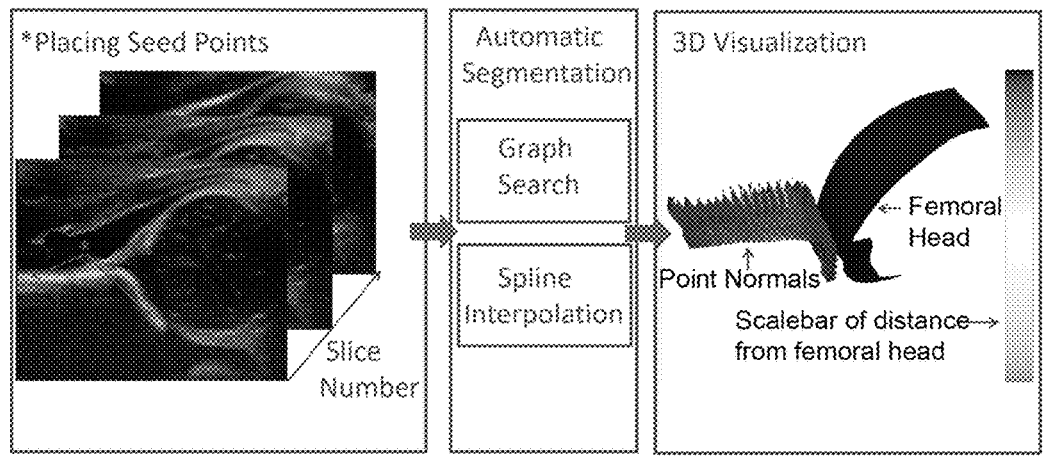
FIG. 2 is a flow diagram illustrating an overview of the semi-automatic segmentation algorithm of the present disclosure.

FIG. 2 is a flow diagram illustrating an overview of the semi-automatic segmentation algorithm of the present disclosure. In some embodiments, the segmentation algorithm of the present disclosure is formulated as a graph search problem. Graph based segmentation techniques have generated considerable research interest in recent years, mainly because graph techniques usually give an exact solution and are non-iterative. The advantage of the graph search based approach is that it is robust to both missing gradients (usually due to shadowing) and noise artifacts (mainly due to speckle noise). In the present disclosure, a cost function for the graph search is proposed that is customized for the acetabular boundary. In the segmentation technique according to the present disclosure, the workflow is initiated by the user clicking on a set of seed points on specific slices. The seed points can be located at terminal points or contour points (e.g., bends, curves, etc.) of the anatomical structure of interest. Based on these seed points, the algorithm performs 2D segmentation on these specific slices and then interpolates the contour over the remainder of the 3D volume.

An overview of the steps in the semi-automatic segmentation technique of the present disclosure is shown in FIG. 2. Particularly, in step 30, the user places the seed points on image slices. Then, in step 32, the images anatomical structure of interest (e.g., acetabulum) is automatically segmented using the graph search based segmentation algorithm of the present disclosure and interpolating the contours of the anatomical structure using cardinal splines. In step 34, a 3D surface model is then generated from the segmented anatomical structure of interest.

Graph Search Based Segmentation Algorithm

Figure 3:
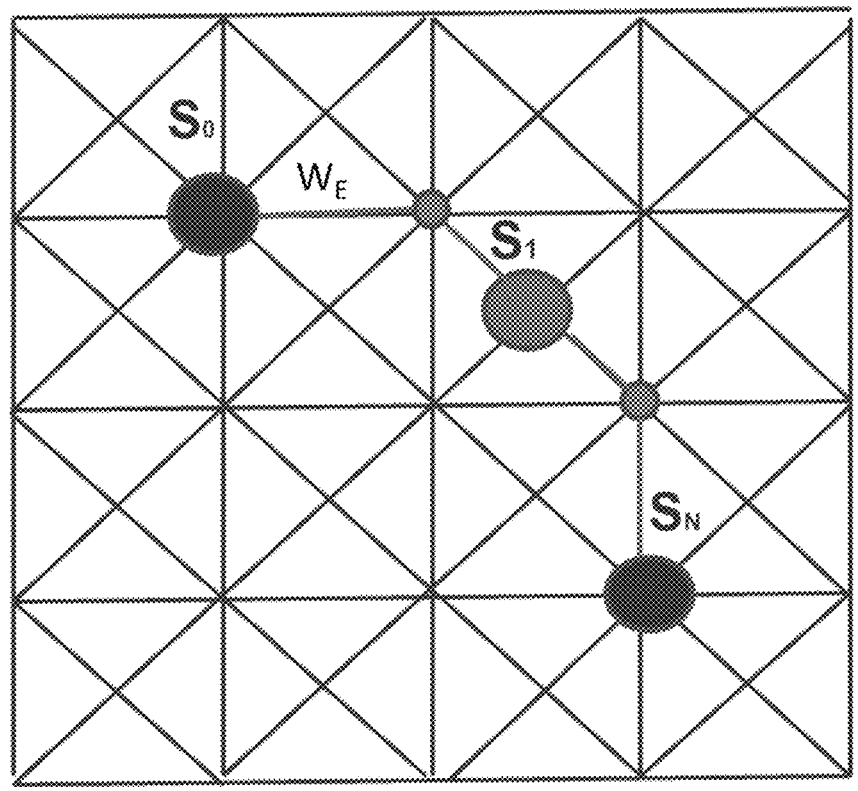
FIG. 3 is a schematic representation of an undirected weighted graph used in a graph search algorithm for boundary definition of an anatomical structure.

Boundary definition of the acetabulum may be formulated as a graph search problem. The algorithm finds the globally optimal path though the set of seed points S on an undirected weighted graph $G=<V, E>$ where V represents the set of vertices and E represents the set of edges on the graph. The optimal path is defined as the minimum cumulative cost path that traverses all the K seed points in S. Each pixel on the image corresponds to a vertex on the graph and is connected to eight neighboring nodes which include vertical, horizontal and diagonal connections. A schematic representation of the graph is shown in FIG. 3.

The intelligent scissors algorithm uses three components to calculate the edge weight, namely Laplacian zero crossing ($f_Z$), Gradient magnitude ($f_G$), and gradient direction ($f_D$). However Laplacian zero crossing might not be present along the edges in noisy ultrasound images. In the present disclosure, a weighting scheme is used that does not use zero crossing. In this scheme, edge weights between nodes p and q on the graph are calculated as follows:

$$W_E = \frac{D_{pq}}{w_1 G_q + w_2 I_q} \quad (1)$$

where $I_p$ and $I_q$ represent the grey level intensity values at pixel positions p and q respectively. $D_{pq}$ represents the squared pixel intensity difference across the edge which can be defined as $$D_{pq} = (I_p - I_q)^2 \quad (2)$$

$G_q$ represents the pixel gradient in the vertical direction which can be computed on the graph as $$G_q = \Delta I_q \quad (3)$$

This formulation ensures low intensity variance along the path due to $D_{pq}$ and also favors bright pixel intensities due to $I_q$ in Equation 1. The vertical gradient $G_q$ is based on the geometry of the acetabulum wherein pixels along the edge have a high vertical gradient. The weights $w_1$ and $w_2$ can be adjusted to vary the effect of the respective terms. So increasing $w_1$ moves the contour towards the edges of the acetabulum while increasing $w_2$ traces the boundary though the center of the echogenic region. Values of $w_1=1$ and $w_2=1$ gave optimal results while testing. The optimal path on the graph can be obtained using dynamic programming techniques such as the Dijkstra's algorithm.

Method of 3D Interpolation

The shortest path from $S_0$ to $S_K$ passing through all the seed points on slice i is denoted by the boundary contour $C_i$. The final segmentation can be obtained by interpolating the contours $C_i$ over the 3D volume using cardinal splines. A variety of other available interpolation methods may also be such as finite differences, Catmull-Rom splines, Kochanek-Bartels splines, and monotone cubic interpolation. For a 3D volume consisting of N slices let set C represent the set of 2D contours segmented from $N_k$ slices such that $N_k \leq N$. A set of cardinal spline interpolants $S_{pk}(z)$ can be defined as $$S_{pk}(z)=(2z^3-3z^2+1)C_i(p)+(z^3-2z^2+z)m_0+(-2z^3+3z^2)C_j(p)+(z^3-z^2)m_1 \quad (4)$$

where $C_i$ and $C_j$ represent the neighboring contours and $C_i(p)$ and $C_j(p)$ represent the end points of the spline. The tangent parameter $m_k$ is defined as $$m_k = (1-c)\frac{C_{k+1}(p) - C_{k-1}(p)}{z_{k+1} - z_{k-1}} \quad (5)$$

where the parameter c is represents the tension on the spline. The formulation of the spline ensures smoothness and continuity over the end points by ensuring that the first and second derivatives are equal i.e $S_{pk}'=S_{p(k+1)}'$ and $S_{pk}''=S_{p(k+1)}''$. It is also assumed that the end points are stationary i.e $S_{pk}(z_0)''=0$ and $S_{pk}(z_{N_c})''=0$.

Calculation Acetabular Contact Angle (ACA)

Figure 4:
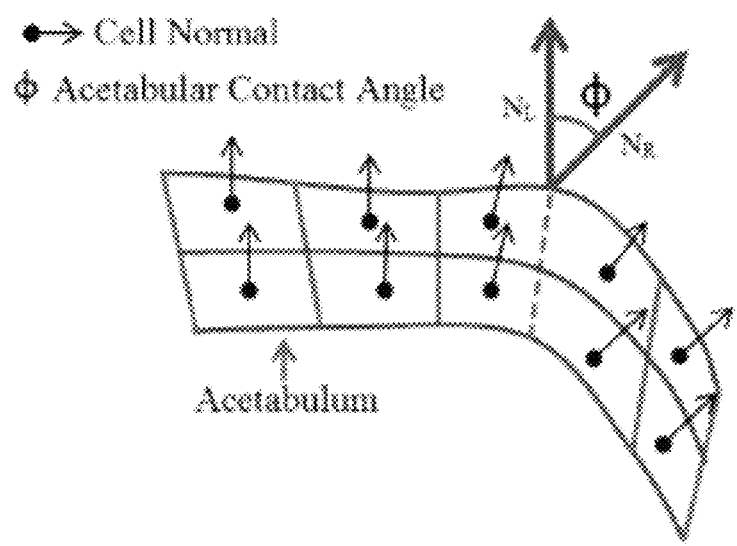
FIG. 4 is a schematic representation showing a polygonal mesh representing a segmented surface for calculation of an acetabular contact angle (ACA).

In order to calculate the Acetabular Contact Angle (ACA) $\Phi$, the segmented surface is represented using a polygonal mesh as shown in FIG. 4. Other models for representing the segmented surface may also be used, such as a network of patches, NURBS, and point sets. Two vectors $N_R$ and $N_L$ are defined corresponding to the lateral iliac wall (to the left of the apex point) and acetabular roof (to the right of the apex point). The vectors $N_R$ and $N_L$ can be represented as the mean values of the cell normals $n_p$ as shown in equations 6 and 7:

$$N_R = \frac{1}{R}\sum_{p=0}^{R} n_p \quad (6)$$

$$N_L = \frac{1}{L}\sum_{p=0}^{L} n_p \quad (7)$$

R and L represent the number of cells to the right and left of the apex point respectively. The locus of the apex points on adjacent slices is represented by the dotted line in FIG. 4. The ACA is defined as the angular separation of the vectors $N_R$ and $N_L$ calculated using the dot product.

Data Acquisition

Fifty-one hips in 42 infants aged from four to 111 days were studied. Three-dimensional ultrasound scanning was added to a routine clinical 2D hip ultrasound scan of each subject. Scan indications were clinical suspicion of DDH due to hip laxity, asymmetric skin creases, and/or risk factors such as positive family history. During the study 3D ultrasound volumes of the hip were obtained using a 13 MHz linear (13VL5) transducer in coronal orientation. The transducer was steered over an angular range of ±15° in 3.2 seconds. Each 3D ultrasound volume acquired for the study comprised of 256 ultrasound slices of 0.13 mm thickness containing 411×192 pixels measuring 0.11×0.20 mm. During the study a total of 51 hips, 27 (64%) females, were analyzed. The average age of the patients was 44.2 days. The patients were categorized into three groups: i) normal at first orthopedic assessment/ultrasound (category 0, 20 hips); ii) questionably abnormal initially but resolved spontaneously on follow-up (category 1, 10 hips); and iii) dysplastic requiring treatment by Pavlik harness and/or surgery (category 2, 21 hips).

Method of 3D Graph Search

The final segmentation could also be obtained using 3D graph search in which the end points of the slice contours are used as seed points for a graph search algorithm in the z dimension (normal to the b-mode plane). Contour points of the shortest path in the z-dimension represented by $C_z$ and can be used as seed points for intermediate slices. The 3D graph based algorithm was able to generate segmented acetabular surface models in less than 50 seconds and the surfaces correlated closely with the actual acetabular contours with RMS error of 1.39±0.7 mm.

Reading Exercise

The inter-observer and intra-observer variability of automatic segmentation against manual segmentation was also compared. Each reader performed two segmentations on each of the 51 hip volumes using manual and automatic segmentation. Two experienced readers, a pediatric musculoskeletal radiologist (XX) and a graduate student with three years dedicated study of 3D hip ultrasound (YY), were involved with the reading exercise. Each reader generated two models for each hip, one using manual segmentation and one using the graph-based segmentation approach, at different reading sessions blinded to the other model and to each other's work. Time preparing each model was noted. The image coordinates were converted to spatial coordinates using the spacing information provided in the image metadata. Variation between each pair of models was measured using the average root mean square (RMS) distance measured for each point on the semi-automatic contour to the closest point on the manual contour and vice-versa.

Results

Figure 5:
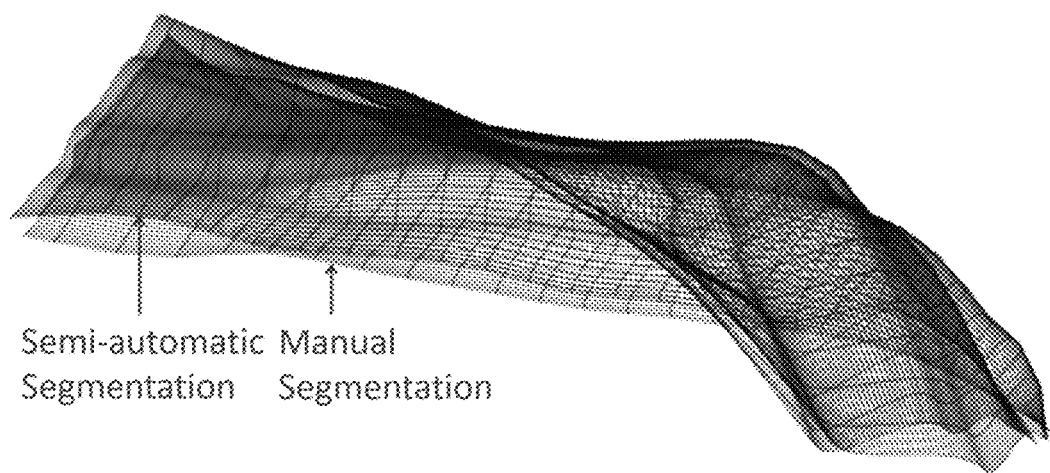
FIG. 5 illustrates three-dimensional models of a manually segmented acetabulum and an acetabulum segmented according to the algorithm of the present disclosure.

The results of the segmentation were compared with corresponding manual tracings of the acetabulum. An example of the semi-automatic segmentation alongside the manual segmentation is shown in FIG. 5.

Figure 6:
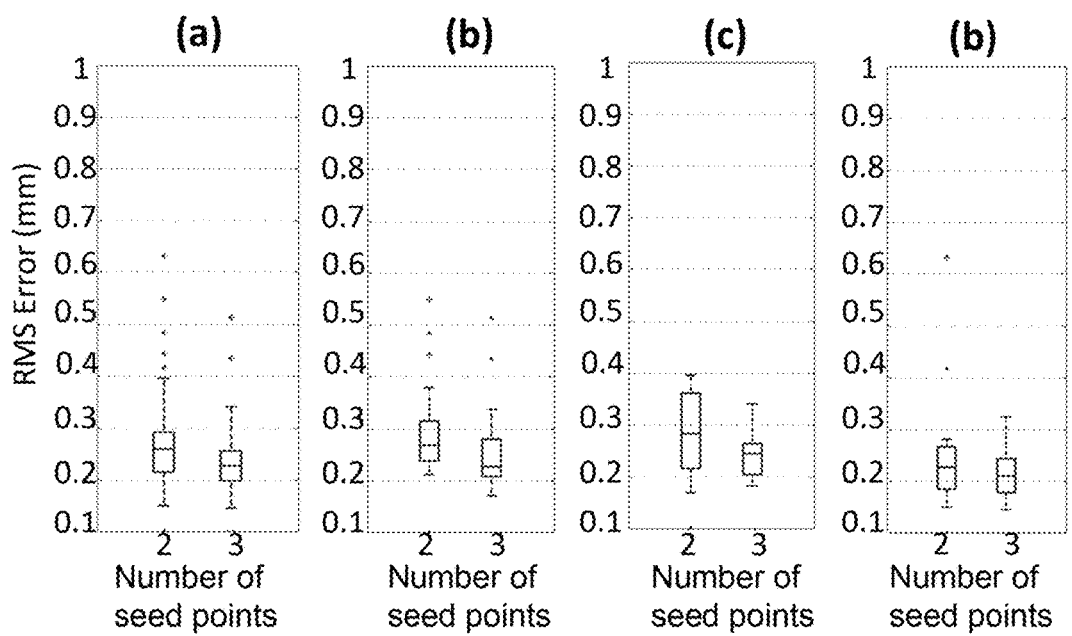
FIGS. 6a-6d are graphs of the RMS error between manual segmentation and segmentation according to the algorithm of the present disclosure, showing (a) overall RMS error, (b) RMS error for normal subjects, (c) RMS error for borderline subjects, and (d) RMS error for dysplastic subject.

Using two end points from the manually traced contours, the semi-automatic technique generated segmentations that closely matched the manual segmentation. Contours were generated on 5-7 slices per recording and these contours were interpolated to get the 3D surface. Contours on the interpolated slices of the 3D surface were modified using a nudge tool and used as the ground truth to quantify the interpolation error. Interpolation error was defined as the mean distance between the refined contour and the original contour. The mean interpolation error was 0.04±0.01 mm. The RMS error in segmentation was defined as the mean of the distance measured from the semi-automatic segmentation to the manual segmentation (without modification) and distance measured from the manual segmentation to the semi-automatic segmentation. The RMS error observed over the 51 datasets had maximum value 0.64 mm, and averaged 0.28 mm. The accuracy of the semi-automated method improved when the apex point of the contour was used as the third seed point. This reduced the maximum and average RMS errors to 0.52 mm and 0.24 mm respectively. The overall RMS error obtained is shown in FIG. 6(*a*). The maximum RMS error obtained for subjects in categories 0, 1 and 2 were 0.55 mm, 0.40 mm and 0.63 mm respectively for two seed points, and 0.51 mm, 0.34 mm and 0.33 mm for three seed points. The corresponding mean values of RMS error were 0.30 mm, 0.29 mm, 0.25 mm and 0.26 mm, 0.24 mm, 0.21 mm. The variation of RMS error for category 0, 1 and 2 are shown in FIGS. 6(*b*), 6(*c*), and 6(*d*), respectively.

Figure 7:
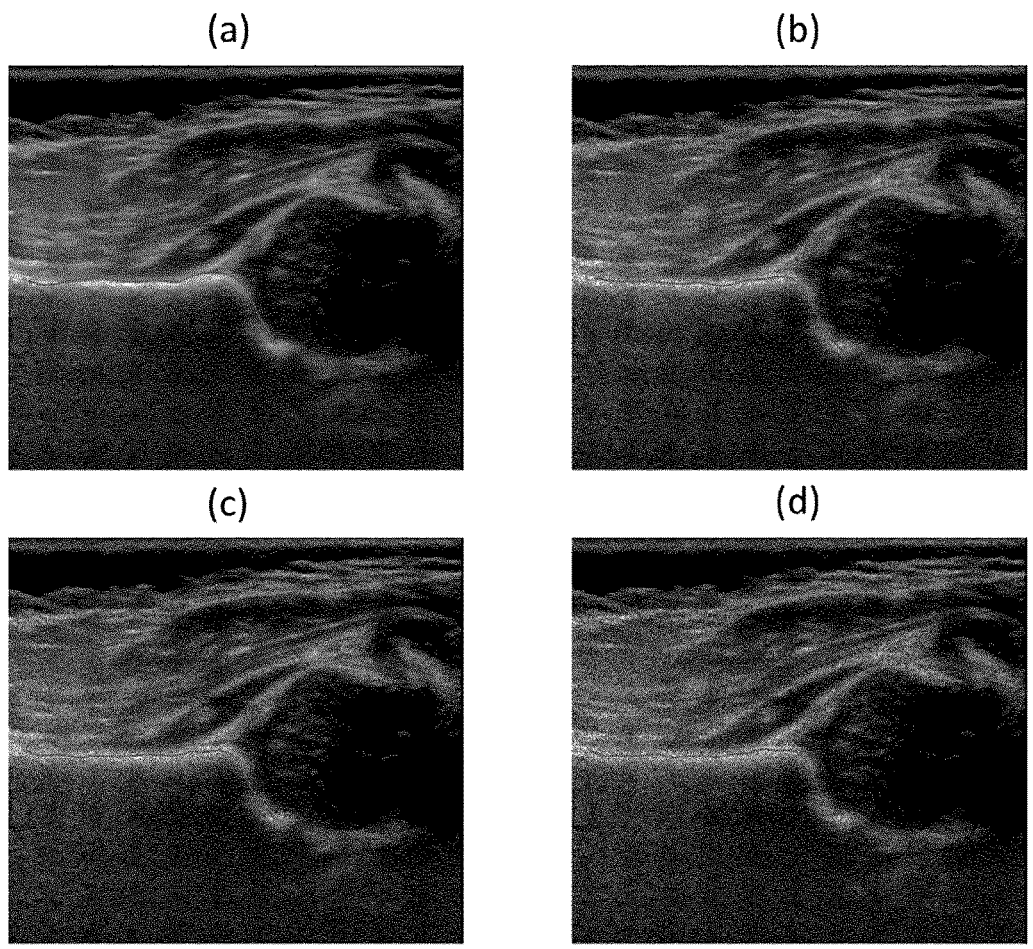
FIGS. 7a-d are images illustrating the effect of speckle noise with different noise variances on the segmentation algorithm of the present disclosure.

The effect of noise on the segmentation algorithm was examined by adding noise to the original image. Multiplicative noise was added to the image as this would roughly simulate the effect of speckles. The noised image $I_N$ was related to the original image I as $$I_N = I + I*n \quad (3)$$

where n is a uniformly distributed zero mean random noise. The variance ($\sigma$) of n was progressively increased from 0.2 to 0.4 in steps of 0.1 so as to increase the noise level of the image. The algorithm was able to segment the boundary of the acetabulum despite the increased noise. The performance of the automatic segmentation algorithm for different values of noise variance ($\sigma$) is shown in FIG. 7.

Figure 8:
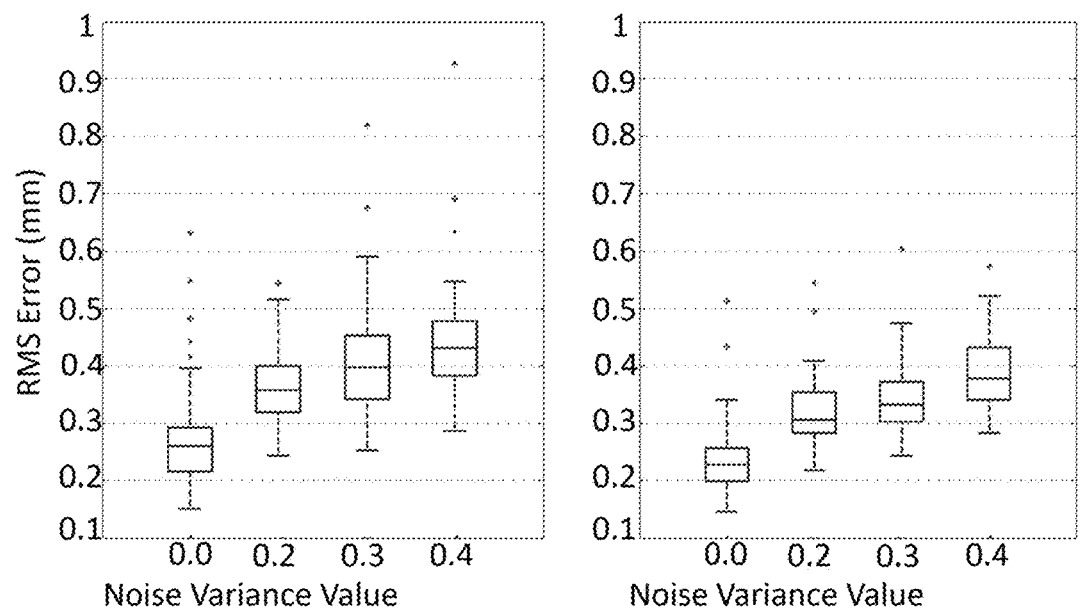
FIGS. 8a and 8b are graphs illustrating the variation in RMS error due to speckle noise in the segmentation algorithm of the present disclosure with two and three seed points, respectively.

The maximum RMS error for noise variance levels of 0.2, 0.3 and 0.4 were 0.54 mm, 0.82 mm and 0.93 mm respectively for two seed points. The corresponding values for three seed points were 0.55 mm, 0.60 mm and 0.57 mm. The variations in RMS error for different levels of speckle noise are shown in FIGS. 8(*a*) and 8(*b*). As indicated in FIGS. 8(*a*) and 8(*b*) the change in mean RMS error was less than 0.2 mm in both cases.

Figure 9:
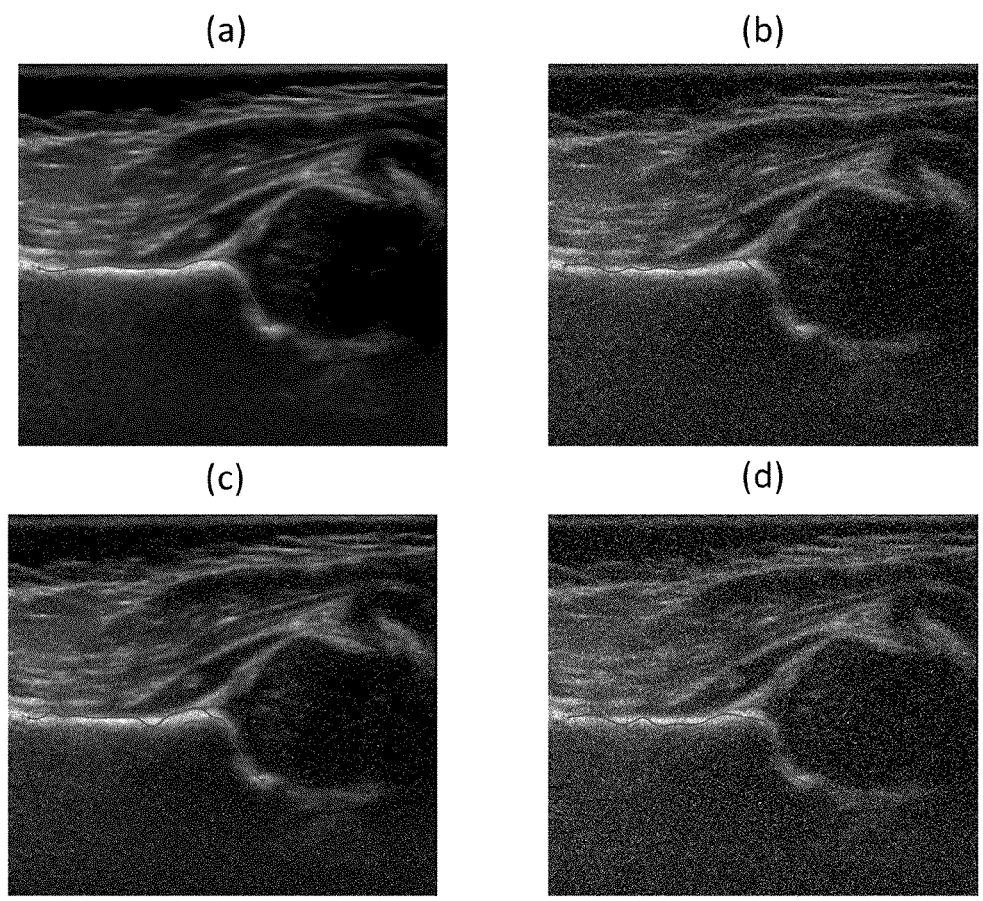
FIGS. 9a-d are images illustrating the effect of "salt and pepper" noise with different percentages on the segmentation algorithm of the present disclosure.

"Salt and pepper" noise was also added to the original image. The percentage of pixels affected by the noise was increased from 5% to 15%. The output of the algorithm was resilient to moderate noise levels, but ripples in the contour were observed at 15% "salt and pepper" noise as shown in FIG. 9(*d*). The effect of various levels of "salt and pepper" noise on the on the automatic segmentation is illustrated in FIG. 9.

Figure 10:
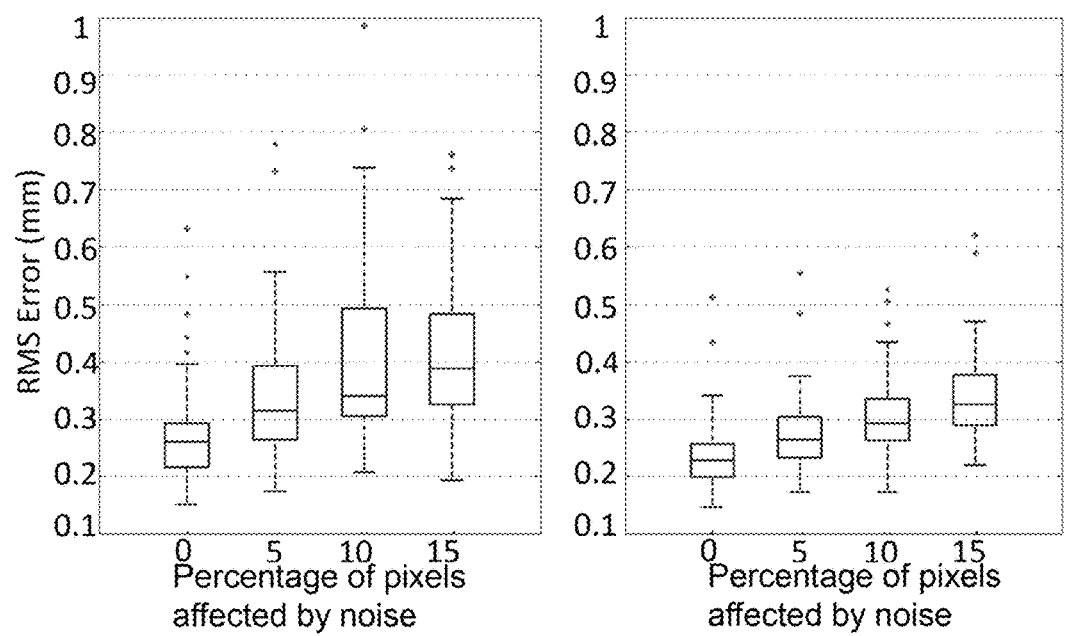
FIGS. 10a and 10b are graphs illustrating the variation in RMS error due to "salt and pepper noise" in the segmentation algorithm of the present disclosure with two and three seed points, respectively.

The maximum RMS error for noise levels of 5%, 10% and 15% were 0.78 mm, 0.99 mm and 1.00 mm respectively for two seed points. The corresponding values for three seed points were 0.56 mm, 0.53 mm and 0.62 mm. The variation in RMS error for different levels of speckle noise are shown in FIGS. 10(*a*) and 10(*b*).

Figure 11:
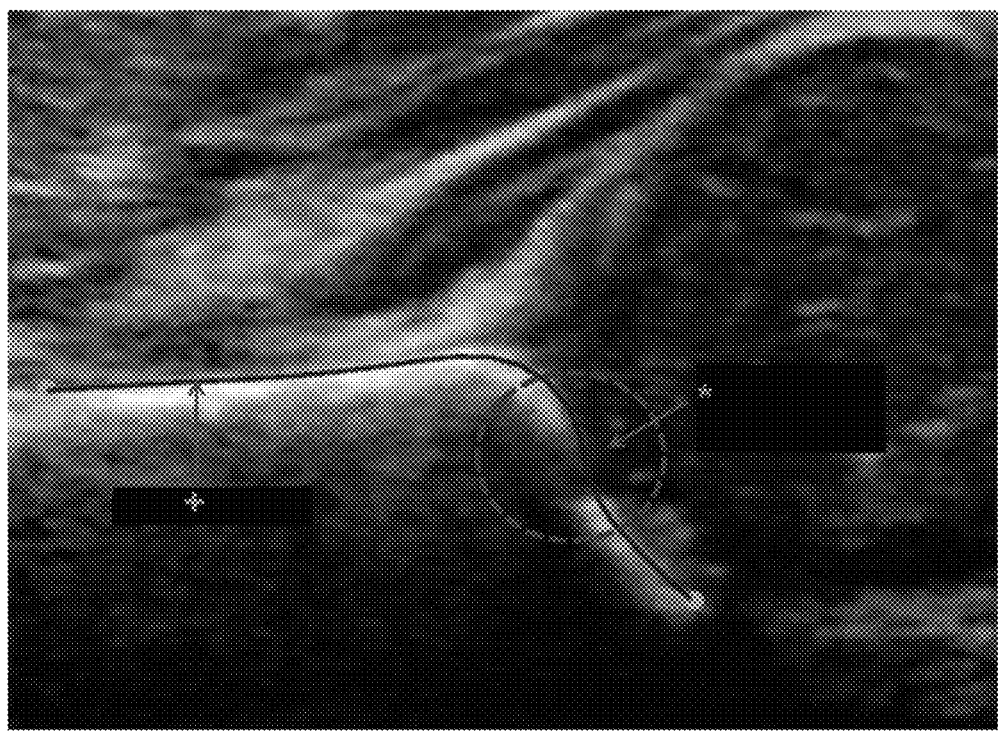
FIG. 11 is an image illustrating the performance of the segmentation algorithm of the present disclosure in the presence of a missing portion of an echogenic boundary.

The performance of the algorithm on images with missing or incomplete boundaries was also tested since such scenarios are very common in medical ultrasound. The automatic algorithm was able to extract the boundary of the acetabulum despite missing edges as illustrated by FIG. 11.

Figure 12:
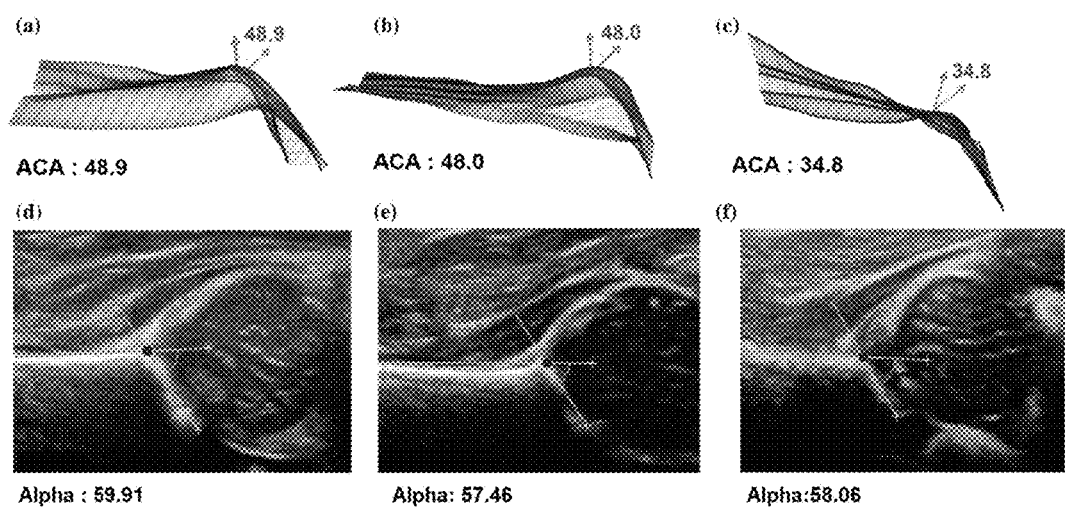
FIGS. 12a-f illustrate a comparison between ACA derived from three-dimensional models generated from the segmentation algorithm of the present disclosure and ACA derived from a conventional alpha angle.

Next the ACA derived from the 3D model was compared with the conventionally used alpha angle. As an example in FIG. 12, the 3D surface model (and the ACA) is shown along with the corresponding alpha angles. FIGS. 12(*a*) and 12(*c*) show 3D models of a normal hip and dysplastic hip with ACA values of 48.9 degree and 34.8 degree. FIGS. 12(*d*) and 12(*f*) show manually delineated acetabular contours obtained from the 2D slices taken from FIGS. 12(*a*) and 12(*c*). The alpha angles in these cases are 59.9 degrees and 58.0 degrees. The large separation in ACA values (48.9 degree and 34.8 degree) and the visible difference in 3D surface model indicate that ACA would be a more reliable indicator for DDH compared to the alpha angle. The borderline case shown in FIG. 12(*b*) gave an ACA value of 48.0 degree and an alpha angle of 57.4 (FIG. 12(*e*)). Hence ACA based classification would correctly classify the borderline case as normal as opposed to the alpha angle which in this case would give ambiguous results.

Evaluation of Repeatability and Processing Time

Figure 13:
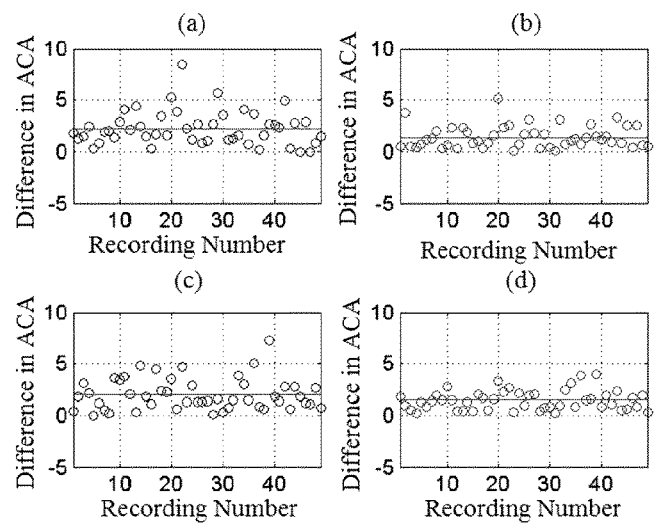
FIGS. 13a-13d are graphs illustrating the intra- and inter-observer variability for manual segmentation and segmentation according to the present disclosure.

The repeatability of the ACA calculation from the 3D surface models was evaluated using the inter-observer and intra-observer variance. The mean intra-observer variance of the manual segmentation was 2.2±1.6 degree while that of the semi-automatic segmentation was 1.4±1.1. Similarly the mean inter-observer variance of manual segmentation was 2.0±1.5 and that of semi-automatic segmentation was 1.4±0.9 degree. The inter-observer and intra-observer differences are represented as scatter plots in FIG. 13.

Figure 14:
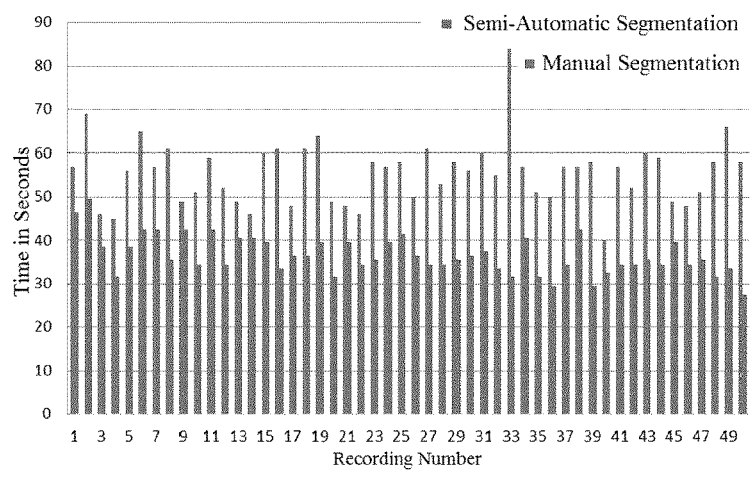
FIG. 14 is a graph illustrating the average processing time taken by an expert user using manual segmentation and segmentation according to the present disclosure.

The average time taken by an expert user for recoding was 56 seconds for the manual segmentation and 37 seconds for automatic segmentation. The processing time for each of the 51 recordings is shown in FIG. 14. The average time taken to generate the 3D model from pre-defined seed points was 11.90 seconds per recording on a 2.30 GHz CPU. The algorithm is also well-suited for parallelization on GPU as the segmentation on individual slices is independent of each other. As illustrated in the FIG. 14 the semi-automatic segmentation was always faster than the corresponding manual segmentation.

This work focused on developing a rapid and practical semi-automatic segmentation algorithm that could be used to delineate complex anatomical structures from a noisy 3D ultrasound volume. The segmentation algorithm was tested on a clinically relevant problem, acetabulum surface modeling from 3D ultrasound of the infant hip. The algorithm is based on optimal path search on a weighted graph and it gives an exact solution in real-time, much faster than typical iterative curve evolution based techniques. The spline interpolation between segmented slices ensured a smooth output surface and is also rapid. Geometric properties of the segmented acetabulum (in the form of acetabular contact angles) were used, which are independent of the femoral head, and the calculation of ACA is based on three dimensional surface normals derived from a polygonal mesh.

The semi-automated segmentation routine produced high-fidelity surface models. When comparing the automatically generated boundaries to manually demarcated boundaries drawn by experts, they were closely matched. The algorithm was also robust to ultrasound noise effects such as shadowing and speckle, in contrast to energy minimization techniques. Other automatic segmentation techniques often fail to produce meaningful edges at non-echogenic "missing" portions of echogenic surfaces. The graph-based search "crosses the gap" in such cases in a robust fashion due to a combination of three terms in the edge weighting calculation making the algorithm well suited for noisy ultrasound volumes. The segmentation is robust to moderate levels of speckle and "salt and pepper" noise. Two seed points (start and finish) were sufficient for images with clearly defined and simple contours, but given the complexity of the typical acetabular edge, modeling error was reduced considerably when the apex point at the junction of ilium and lateral acetabulum was also included as a third seed point. Also in images with very high levels of noise two seed points were found to be insufficient. Out of the three categories of subjects analysed the RMS error was minimum in dysplastic hips (i.e., category 2), likely because in these hips the acetabular contour is a smoothly varying curve rather than the sharp edge seen in normal hips.

The ACA derived from the surface model showed a clear distinction between normal and dysplastic hips and was able to classify the subjects into the three categories. The ACA was also able to classify most of the borderline cases as normal which was eventually diagnostically correct. This is promising because one goal of 3D ultrasound in hip dysplasia is to eliminate costly and redundant follow-up imaging for patients. The ACA calculated using the semi-automated segmentation showed better repeatability than the manual segmentation. Both inter-observer and intra-observer mean variations were less than 1.5 degrees for the automatic approach. The automated segmentation also reduced the expert time need to per recording by approximately 34%.

Although the automated segmentation technique of the present disclosure has been applied to the infant acetabulum in 3D hip ultrasound, the technique could be generalized for any 3D or 2D+t ultrasound data set. For example the proposed technique could be used for segmentation of the myocardial wall in echocardiograms, the walls of the carotid artery, margins of a tumor, or the borders of an abdominal organ such as liver or kidney.

In sum, the graph-based automatic segmentation technique of the present disclosure offers a fast and reliable method to delineate the 3D surface and shape of the acetabulum from 3D ultrasound volumes of an anatomical structure of interest. The method gives an exact solution and requires very few user-identified points. It also offers robust handling of noisy data with "missing" echogenic boundaries common in ultrasound, since the technique does not rely upon contour evolution. The Acetabular Contact Angle (ACA) derived from this segmented surface models better discriminated between dysplastic and normal hips than 2D methods. Graph-based surface modeling was highly reliable within 1.4±1.1 degree and 1.4±0.9 degrees inter-observer and intra-observer variation, respectively. Hence the surface models and ACA generated by this method may be used in more accurate diagnosis of hip dysplasia. This method can also be generalized to delineate the contours of any structure with an echogenic border on any 3D or 2D+t ultrasound dataset, or any structure with a bright border on computed tomography or magnetic resonance imaging.

Additional information regarding the systems and methods of the present disclosure is provided in Appendices A and B attached hereto.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

What is claimed is:

1. A system for segmenting an anatomical structure from a plurality of images generated in an anatomical scan, the system comprising:
   a user input device configured for manually identifying two or more seed points on a plurality of the images; and
   an image processor configured to identify an optimal path through seed points on the plurality of images with a graph search, the optimal path between corresponding seed points on different images defining a boundary contour, wherein the anatomical structure includes two or more boundary contours, the image processor further configured to interpolate the boundary contours over a three-dimensional volume.

2. The system of claim 1, wherein the image processor is configured to use cardinal splines to interpolate the boundary contours over the three-dimensional volume.

3. The system of claim 2, wherein the anatomical structure is an acetabulum.

4. The system of claim 3, wherein the image processor is further configured to represent a surface of the three-dimensional volume and define a first vector on the surface corresponding to a lateral iliac wall and a second vector on the surface corresponding to an acetabular roof, the image processor further configured to calculate an acetabular contact angle (ACA) based on an angular separation between the first and second vectors.

5. The system of claim 4, wherein the surface of the three-dimensional volume is represented using a polygonal mesh.

6. A method for segmenting an anatomical structure from a plurality of images generated in an anatomical scan, the method comprising:
   receiving the anatomical scan images including two or more seed points identified on a plurality of the images;
   identifying an optimal path through seed points on a plurality of the images with a graph search, the optimal path between corresponding seed points on different images defining a boundary contour, wherein the anatomical structure includes two or more boundary contours; and
   interpolating the boundary contours over a three-dimensional volume.

7. The method of claim 6, wherein cardinal splines are used to interpolate the boundary contours over the three-dimensional volume.

8. The method of claim 7, wherein the anatomical structure is an acetabulum.

9. The method of claim 8, the method further comprising:
   representing a surface of the three-dimensional volume and define a first vector on the surface corresponding to a lateral iliac wall and a second vector on the surface corresponding to an acetabular roof; and
   calculating an acetabular contact angle (ACA) based on an angular separation between the first and second vectors.

10. The method of claim 9, wherein the surface of the three-dimensional volume is represented using a polygonal mesh.

11. A method for determining an acetabular contact angle (ACA), the method comprising:
   segmenting images of a scan of an acetabulum according the method of claim 6;
   representing a surface of the three-dimensional volume;
   defining a first vector on the surface corresponding to a lateral iliac wall and a second vector on the surface corresponding to an acetabular roof; and
   calculating the acetabular contact angle (ACA) based on an angular separation between the first and second vectors.

12. The method of claim 11, wherein the surface of the three-dimensional surface is represented using a polygonal mesh.

13. A method for diagnosing hip dysplasia in a patient, the method comprising:
   determining the acetabular contact angle (ACA) of the patient according to the method of claim 12;

classifying the patient's hip based on the acetabular contact angle (ACA); and
diagnosing the patient based on the classification.

* * * * *